United States Patent [19]

Morris

[11] Patent Number: 4,851,592

[45] Date of Patent: Jul. 25, 1989

[54] TRIETHYLAMINE CATALYZED NEOPENTYL GLYCOL PRODUCTION UTILIZING A GAS SPARGED REACTOR

[75] Inventor: Don L. Morris, Longivew, Tex.

[73] Assignee: Eastman Kodak Company, Rochester, N.Y.

[21] Appl. No.: 113,049

[22] Filed: Oct. 27, 1987

[51] Int. Cl.$^4$ .................. C07C 29/14; C07C 31/20
[52] U.S. Cl. ..................... 568/853; 568/461
[58] Field of Search ......................... 568/853

[56] References Cited

U.S. PATENT DOCUMENTS

| | | | |
|---|---|---|---|
| 2,761,881 | 9/1956 | Rosin | 260/635 |
| 2,778,858 | 1/1957 | Meinhofer | 260/635 |
| 2,786,083 | 3/1957 | Wyler | 260/635 |
| 2,811,562 | 10/1957 | Hagemeyer, Jr. | 260/602 |
| 2,865,819 | 12/1958 | Hagemeyer, Jr. | 202/42 |
| 2,895,996 | 7/1959 | Wright, Jr. et al. | 260/637 |
| 3,088,982 | 5/1963 | Feldman et al. | 260/637 |
| 3,168,579 | 2/1965 | Boswell, Jr. et al. | 260/635 |
| 3,340,312 | 9/1967 | Duke, Jr. et al. | 260/635 |
| 3,483,264 | 12/1969 | Tsao | 260/637 |
| 3,504,042 | 3/1970 | Shimono et al. | 260/635 |
| 3,652,458 | 3/1972 | Gobron et al. | 252/454 |
| 3,808,280 | 4/1974 | Merger et al. | 260/635 |
| 3,920,760 | 11/1975 | Heinz | 260/635 A |
| 3,935,274 | 1/1976 | Jacobsen et al. | 260/602 |
| 3,939,216 | 2/1976 | Wright | 260/635 |
| 3,975,450 | 8/1976 | Palmer et al. | 260/635 |
| 4,032,578 | 6/1977 | Savini | 260/601 |
| 4,036,888 | 7/1977 | Couderc | 260/602 |
| 4,038,329 | 7/1977 | Palmer et al. | 260/637 |
| 4,094,914 | 6/1978 | Rottig et al. | 568/862 |
| 4,097,540 | 6/1978 | Immel et al. | 568/862 |
| 4,122,290 | 10/1978 | Immel et al. | 568/853 |
| 4,153,578 | 5/1979 | De Thomas et al. | 252/438 |
| 4,250,337 | 2/1981 | Hausen et al. | 568/853 |
| 4,298,766 | 11/1981 | Broecker et al. | 568/862 |
| 4,386,219 | 5/1983 | Merger et al. | 568/853 |

FOREIGN PATENT DOCUMENTS

| | | |
|---|---|---|
| 0008767 | 3/1980 | European Pat. Off. . |
| 138607 | 11/1976 | Japan . |
| 783458 | 9/1957 | United Kingdom . |
| 1219162 | 1/1971 | United Kingdom . |

OTHER PUBLICATIONS

Chem. Zeitung, 100(12), 504 (1976).

*Primary Examiner*—J. E. Evans
*Attorney, Agent, or Firm*—Thomas R. Savitsky; William P. Heath, Jr.; Mark A. Montgomery

[57] ABSTRACT

A process for producing neopentyl glycol is disclosed which comprises reacting isobutyraldehyde and formaldehyde in the presence of a trialkylamine catalyst to form a condensation reaction product comprising hydroxypivaldehyde, followed by hydrogenation of the hydroxypivaldehyde in a hydrogen gas sparged reactor in the presence of a Raney nickel catalyst. This process minimizes unwanted by-products, and does not have to be carried out under high pressure as do certain prior art methods.

17 Claims, No Drawings

4,851,592

TRIETHYLAMINE CATALYZED NEOPENTYL GLYCOL PRODUCTION UTILIZING A GAS SPARGED REACTOR

FIELD OF THE INVENTION

The invention relates to a method for producing neopentyl glycol.

BACKGROUND OF THE INVENTION

Neopentyl glycol (hereinafter "NPG") is an important starting material for the preparation of various useful products such as lubricants, plastics, surface coatings and synthetic resins. NPG has commonly been produced by effecting an aldol condensation of isobutyraldehyde and formaldehyde, followed by the hydrogenation of the condensation product, hydroxypivaldehyde. One type of aldol catalyst used with these reactions has been an alkali metal-containing catalyst, such as sodium carbonate. However, these catalysts produce a condensation product containing a high amount of undesirable carboxylic acid salts, which must be removed prior to hydrogenation. Additionally, use of sodium-based aldol catalysts can jeopardize the effectiveness of a hydrogenation catalyst such as Raney nickel. The successful use of the Raney nickel hydrogenation catalyst requires the removal of the sodium prior to hydrogenation in order to prevent deactivation of the catalyst, or decomposition of the hydroxypivaldehyde to formaldehyde, which will poison the nickel catalyst.

Other catalysts useful in producing the aldol condensation product of isobutyraldehyde and formaldehyde are tertiary amines, such as those described in U.S. Pat. No. 3,808,280. Although the use of tertiary amines has provided high yields of the desired hydroxypivaldehyde, with low levels of by-products such as isobutyraldoxane and NPG isobutyrate, there by-products must be stripped from the hydroxypivaldehyde before hydrogenation to the NPG product, because they form impurities upon hydrogenation, such as 2,2,4-trimethyl-1,3-pentanediol (TMPD) and isobutanol, which are very difficult to remove from the ultimate NPG product. Additionally, the hydrogenation of hydroxypivaldehyde crude product produced by the aldol condensation reaction must be carried out at high pressures, e.g., 4,000 psig, or excessive by-product formation results. This by-product formation occurs largely because residual tertiary amine catalyst is present in the hydroxypivaldehyde crude product, and tends to cause decomposition thereof during the hydrogenation, producing decomposition products that lower total NPG production and increase unwanted impurities, such as isobutanol. Simultaneously, the residual tertiary amine catalyst and decomposition products tend to rapidly deactivate or poison the hydrogenation catalyst. Heretofore, in order to avoid this high by-product formation it has been necessary to remove the residual catalyst and decomposition products prior to the hydrogenation, or conduct the hydrogenation under high pressures.

It is thus desirable to have a process which can maximize yield of NPG and minimize formation of unwanted impurities. It is further desirable to perform this production with a minimum of steps, and without the need to conduct the reaction at high pressures.

SUMMARY OF THE INVENTION

It has now been discovered that high yields of neopentyl glycol can be obtained in the hydrogenation of tertiary amine catalyst produced hydroxypivaldehyde crude product without first stripping the hydroxypivaldehyde crude product free of catalyst residue, and without the need of high pressures in the hydrogenation, provided the hydrogenation is conducted in a hydrogen gas sparged reactor using a Raney nickel catalyst. Use of the gas sparged reactor design in this hydrogenation reaction has been found to achieve the desired high yields because it rapidly strips tertiary amine catalyst-containing residues from the reactor during the hydrogenation. This stripping action maintains the tertiary amine catalyst residues in the reactor at very low concentrations thereby minimizing the decomposition of hydroxypivaldehyde, and allowing for greater yield of NPG from the hydroxypivaldehyde. For this reason, and unlike prior art methods, the process of the invention allows for the production of high yields of NPG and reduced by product formation without the necessity of purifying the crude hydroxypivaldehyde product prior to hydrogenation and/or conducting the hydrogenation under high pressures.

DETAILED DESCRIPTION OF THE INVENTION

The process of the present invention is desirably carried out in two basic parts; first, isobutyraldehyde and formaldehyde are reacted in the presence of a trialkylamine catalyst and undergo a condensation reaction which produces hydroxypivaldehyde; then, the hydroxypivaldehyde is hydrogenated in a hydrogen gas sparged reactor in the presence of a Raney nickel catalyst to produce NPG. It is preferred that this process be carried out using a reactor designed to operate continuously.

The first step of the invention is preferably carried out in an aldol reactor into which is fed formaldehyde, and a $C_1$–$C_4$ trialkylamine (TAA) catalyst. The most preferred TAA is triethylamine (TEA). The aldol reactor used is preferably a "pump around" reactor which provides mixing of the reagents. It is desirable to react these components in an aqueous solution with the formaldehyde being preferably introduced into the reactor as a 30 to 50 percent aqueous solution. Isobutyraldehyde is pumped in as a liquid, and if desired, can be mixed with the TAA catalyst before introduction into the reactor. The ratio of isobutyraldehyde to formaldehyde should be maintained at from 1:1 to about 1.5:1, and this can be done by adjusting the feed rates to the aldol reactor. The amount of TAA catalyst needed is variable, but the total amount of TAA generally comprises from about 0.1 to about 2 percent of the reaction mixture.

The aldol condensation reaction is carried out at temperatures from about 80° C. to about 100° C., and a 15–25 psig nitrogen pressure is applied to ensure that the reactants will be kept in liquid form. A residence time of anywhere from about half an hour to about one hour is usually sufficient to effect the condensation reaction. The aldol reactor can be staged to improve its efficiency.

The formaldehyde is converted to hydroxypivaldehyde product at an efficiency of from 95% to 100% in the aldol reactor and the hydroxypivaldehyde produced in this reactor will contain other materials such as some unreacted isobutyraldehyde as well as some unused TAA catalyst and TAA-containing residues. Most of these are preferably removed from the solution by distillation involving use of a recovery column arranged to return the components to the aldol reactor. Nevertheless, the crude hydroxypivaldehyde product of the aldol condensation reaction will be mostly hydroxypivaldehyde (about 60%–80%) and water (about 10%–35%) with minor but significant amounts of TAA and TAA-containing residues such as trialkylammonium formate, hydroxypivalyl hydroxypivalate, NPG isobutyrate, isobutyraldehyde, trialkylammonium hydroxypivalate, and trialkylammonium isobutyrate. When TEA is used as the TAA catalyst, the TEA-containing residues will contain compounds such as triethylammonium formate, triethylammonium hydroxypivalate, and triethylammonium isobutyrate; with triethylammonium formate predominating. The amount of TAA and TAA-containing residues in the crude hydroxypivaldehyde product feed is typically up to about 1% by weight.

The hydroxypivaldehyde crude product so obtained is then subjected to the second step of the invention. This second step can be viewed separately as an invention apart from the first step. The hydroxypivaldehyde crude product is introduced into a hydrogen gas sparged reactor. By a "hydrogen gas sparged reactor" as used herein and in the appended claims is meant a reactor designed so that hydrogen flows through the reactor at a given rate. In the preferred design, hydrogen enters at the bottom of the reactor and exits through the top. The liquid level in the reactor should be maintained at a substantially constant level by the stripping action of the hydrogen gas. Introduced into the liquid crude hydroxypivaldehyde is a Raney nickel hydrogenation catalsyt. Raney nickel catalysts are highly active hydrogenation catalysts prepared by leaching aluminum from a nickel aluminum alloy with caustic. Activated catalysts are pyrophoric because of hydrogen absorbed on the nickel surface. The catalysts are sometimes promoted by incorporating various metals such as molybdenum, in order to increase the reaction efficiency. Catalysts of this type are described in *Reagents for Organic Synthesis* by Louis and Mary Fieser, p. 723, Vol. 1, 1967, John Wiley and Sons, Inc. The amount of Raney nickel catalyst employed generally varies from about 0.1 to about 20 percent of the hydroxypivaldehyde. It is particularly preferred that the Raney nickel be about 2% to 10% by weight of the hydroxypivaldehyde. When a promoted Raney nickel catalyst is used, the preferred amount is from 0.5% to about 8% by weight of the hydroxypivaldehyde.

It is preferred that the gas sparged reactor be maintained at a temperature of from 140° to 180° C., and that a hydrogen pressure of from about 40 to 120 pounds per square inch gauge (psig) be applied. The hydrogenation reaction residence time should be in a range of about 1–6 hours. The hydrogen sparger is maintained at sufficient flow to strip NPG, $H_2O$, TAA and TAA-containing residues from the reactor. Generally, keeping a constant level of liquid reaction mixture provides more than enough sparge to sufficiently strip the nitrogen-containing products (which include TAA and TAA-containing residues). Normally a flow rate of 1–1.5 pounds an hour of $H_2$ per pound of feed has proved satisfactory. The ratio of liquid volume to fresh feed is maintained at from 6:1 to 1:1. The concentration of nitrogen-containing residues (including TAA and TAA-containing residues) in the liquid inside the gas sparged reactor is typically less than 0.1% by weight, and preferably less than 0.01%. Surprisingly, the TAA and TAA-containing residues are rapidly removed from the liquid phase of the gas-sparged reaction mixture and maintained at a low concentration by the sparging action. The gas streams containing the reaction products are passed through a vapor/liquid separator, and the liquid-containing crude NPG is recovered for distillation. The gas in the separator is recycled to the hydrogenation reactor. The crude NPG liquid product will contain 60–70 weight percent NPG, 20–30 weight percent $H_2O$, and minor amounts of isobutanol, methanol, TAA, TAA-containing residues, hydroxypivalyl, hydroxypivalate, and isobutyrate.

This crude NPG product can then be treated with sodium hydroxide to liberate any remaining TAA from carboxylic acid salts and to saponify any ester by-products. Sodium hydroxide should be introduced in amount equal to about 1 pound per 100 pounds of NPG at a temperature of about 90° C. The NPG stream is then distilled to remove isobutanol, methanol, TAA and $H_2O$ at a temperature of about 100° C. and a pressure of 760-mmHg. The NPG/$H_2O$ mixture can then be further distilled from sodium containing salts by flash distillation at temperatures from 140° to 160° C. and at pressures from 90 mmHg to 130 mmHg. If necessary, further distillation to remove remaining $H_2O$ can be undertaken. Optionally a 90% to 95% yield of NPG from isobutyraldehyde and an 88% to 93% yield from formaldehyde is obtained. The NPG will contain only trace amounts of impurities, such as 2,2,4-trimethyl-1,3-pentanediol (TMPD), and has a melting point of 128° to 130° C. The TAA catalyst recovered in the distillation process can be reused in the aldol reaction.

The invention is further illustrated in the following specific example:

EXAMPLE 1

Continuous Synthesis of Neopentyl Glycol (NPG)

This example demonstrates the synthesis of NPG using the process described in this invention in a bench-scale aldol reactor designed to operate continuously. Isobutyraldehyde is mixed with 2 weight percent TEA prior to being fed to the aldol reactor. Formaldehyde is fed to the aldol reactor as a 44 percent aqueous solution. The aldol reactor is a "pump around" reactor which provides mixing of the reagents and a residence time of 1 hour. The aldol reactor can be staged to improve its efficiency. The aldol reactor is operated at 90° C. under 15 psig nitrogen pressure (enough pressure to keep the reactants as liquids). The formaldehyde is 90 to 100 percent converted to products in the aldol reactor. The ratio of isobutyraldehyde/formaldehyde is maintained at 1.1/1 to 1.2/1 by adjusting the feed rates to the aldol reactor. The crude hydroxypivaldehyde leaving the aldol reactor contains unreacted isobutyraldehyde and unused TEA catalyst which is removed in the isobutyraldehyde recovery column and returned as feed to the aldol reactor. Methanol is an impurity in this stream which is present in the formaldehyde solution. The crude hydroxypivaldehyde leaving the isobutyraldehyde recovery column contains 27 weight percent water, 0.5 to 1.0 percent triethylammonium formate, 69 percent hydroxypivaldehyde, 2 percent hydroxypivalyl hydroxypivalate (HPHP), 0.2 percent NPG isobutyrate, and traces of isobutyraldehyde. This material is fed to a gas sparged hydrogenation reactor designed to allow hydrogen to enter the bottom of the reactor and exit through the top. The liquid in the reactor is maintained at a constant level by the stripping action of the hydrogen gas. The liquid contains 2 to 10 weight percent Raney nickel. The reactor is maintained at 140° to 180° C. and 40 to 120 psig of hydrogen pressure. The ratio of liquid volume to fresh feed is maintained at between 6/1 and 1/1. The gas streams leaving the reactor pass through a vapor/liquid separator. The gas is recycled to the hydrogenation reactor and the lquid consisting of 27 weight percent $H_2$, 2 percent isobutanol, 1 percent methanol, 0.5 to 1.0 percent TEA, 2 percent HPHP, 0.2 percent NPG isobutyrate, and 67 percent NPG is treated with sodium hydoxide, 1 pound per 100 pounds of NPG, at 90° C. The crude NPG stream is then distilled to remove isobutanol, methanol, TEA, and $H_2O$ at 100° C. and 760 mmHg. The NPG/$H_2O$ mixture is flash distilled from sodium containing salts at 150° C. and 130 mmHg. A final distillation to remove $H_2O$ produces NPG is 94 percent yield from isobutyraldehyde and 91 percent yield from formaldehyde. The NPG contains 0.3 weight percent TMPD and traces of other impurities. It has a melting point of 128° to 130° C. Isobutanol is obtained in 3.5 percent yield by distillation of the low boiling products. Triethylamine is reused in the aldol reaction.

EXAMPLE 2

Hydrogenation of Hydroxypivaldehyde Without Gas Sparging

Hydroxypivaldehyde prepared in the same manner as Example 1 and containing 1.0 percent triethylammonium formate is hydrogenated at 500 psig hydrogen pressure over Raney Ni. The hydrogen is maintained at a constant pressure but is not sparged through the reactor. The reactor is held at 140° C. The crude organic product contains 47.4 percent NPG, 26 percent unreacted hydroxypivaldehyde, 26 percent hydroxypivalyl hydroxypivalate, and 8 percent isobutanol indicating that the catalyst loses activity.

A control run using triethylammonium formate free hydroxypivaldehyde produces a gas organic product containing 3.8 percent isobutanol, 85 percent NPG, and 5 percent hydroxypivalyl hydroxypivalate.

What is claimed is:

1. A process for producing neopentyl glycol comprising reacting isobutyraldehyde and formaldehyde in the presence of a trialkylamine catalyst to form a reaction product comprising hydroxypivaldehyde, and hydrogenating said hydroxypivaldehyde reaction product in a hydrogen gas sparged reactor in the presence of a Raney nickel catalyst.

2. A process according to claim 1 wherein the isobutyraldehyde and formaldehyde are reacted in an aqueous solution.

3. A process according to claim 2 wherein the formaldehyde is introduced into the reaction as an aqueous solution comprising about 30 to 50 percent formaldehyde.

4. A process according to claim 1 wherein the trialkylamine catalyst comprises about 0.1 to 2 percent by weight of the isobutyraldehyde and formaldehyde reaction mixture.

5. A process according to claim 1 wherein the trialkylamine catalyst is triethylamine.

6. A process according to claim 4 wherein the trialkylamine catalyst is triethylamine.

7. A process according to claim 1 wherein the reaction of isobutyraldehyde and formaldehyde is carried out at a temperature of about 80° to 100° C.

8. A process according to claim 1 wherein the Raney nickel catalyst comprises from about 0.1 to 20 percent of the hydroxypivaldehyde.

9. A process according to claim 1 wherein the Raney nickel catalyst is promoted with molybdenum.

10. A process according to claim 9 wherein the molybdenum-promoted Raney nickel catalyst comprises about 0.5 to 8 percent of the hydroxypivaldehyde.

11. A process according to claim 1 wherein the hydrogenation reaction is carried out at a temperature from about 140° to 180° C. for about 1 to 6 hours under a hydrogen pressure of about 40 to 100 psig.

12. A continuous process for producing neopentyl glycol comprising hydrogenating a feed reaction product comprising about 60 to 80 percent by weight hydroxypivaldehyde, about 10 to 35 percent by weight water and about 1 percent by weight of trialkylamine and trialkylamine-containing residues in a reactor under a hydrogen gas sparge sufficient to keep the reaction mixture in the reactor at substantially a constant level, said hydrogenating occurring in the presence of a Raney nickel catalyst.

13. A process according to claim 12 wherein said trialkylamine catalyst is triethylamine.

14. A process according to claim 12 wherein the concentration of trialkylamine and trialkylamine-containing residue in the reaction mixture is about 0.01 percent by weight.

15. A process according to claim 12 wherein the concentration of Raney nickel catalyst in the reaction mixture comprises from about 0.1 to 20 percent of the hydroxypivaldehyde.

16. A process according to claim 12 carried out at a temperature from about 140° to 180° C. for about 1 to 6 hours and under a hydrogen pressure of about 40 to 100 psig.

17. A process according to claim 12 wherein the Raney nickel catalyst is molybdenum promoted and is present in an amount from about 0.5 to 8 percent by weight of the hydroxypivaldehyde.

* * * * *